United States Patent [19]
Jacobson

[11] Patent Number: 5,905,169
[45] Date of Patent: May 18, 1999

[54] PROCESS FOR PRODUCING POLYFLUOROACYL COMPOSITIONS

[75] Inventor: Stephen Ernest Jacobson, Princeton Junction, N.J.

[73] Assignee: E. I. Du Pont De Nemours and Company, Wilmington, Del.

[21] Appl. No.: 08/406,617

[22] Filed: Mar. 20, 1995

[51] Int. Cl.$^6$ .................................................. C07C 51/58
[52] U.S. Cl. .................... 562/851; 562/856; 562/859; 562/860; 562/861; 562/541
[58] Field of Search ..................................... 562/851, 856, 562/859, 860, 861, 541

[56] References Cited

U.S. PATENT DOCUMENTS

| | | | |
|---|---|---|---|
| 2,922,816 | 1/1960 | Bruce, Jr. ................................ | 260/544 |
| 3,883,407 | 5/1975 | Dittman ................................... | 204/158 |
| 4,022,824 | 5/1977 | Childs ...................................... | 260/539 |
| 5,041,647 | 8/1991 | Gotoh et al. ............................ | 562/605 |
| 5,241,113 | 8/1993 | Jacobson ................................. | 562/543 |
| 5,296,640 | 3/1994 | Jacobson et al. ....................... | 562/856 |

FOREIGN PATENT DOCUMENTS 0 638 539   2/1995   European Pat. Off. .

OTHER PUBLICATIONS

European Search Report.

*Primary Examiner*—José G. Dees
*Assistant Examiner*—Rosalynd Williams

[57] ABSTRACT

A process is disclosed for preparing polyhaloacyl fluorides such as trifluoroacetyl fluoride and difluoroacetyl fluoride by oxidizing 1-chloro-1,2,2,2-trifluoroethanes and 1,1-dichloro-2,2-difluoroethane, respectively with oxygen.

12 Claims, No Drawings

PROCESS FOR PRODUCING POLYFLUOROACYL COMPOSITIONS

CROSS-REFERENCE TO RELATED PATENT

The instant invention is related to U.S. Pat. No. 5,296,640, which issued on Mar. 22, 1994 in the names of Jacobson and Ely, entitled "Process For Preparing Perhalocyl Chlorides" (corresponding to PCT Publication No. WO94/06742); the disclosure of which is hereby incorporated by reference.

FIELD OF THE INVENTION

The instant invention relates to an oxidative process for producing polyfluoroacyl fluorides, chlorides and free acids thereof. More particularly, the instant invention relates to a process which comprises oxidizing at least one polyfluoroalkyl-substituted dichloro- or chlorofluoromethane. One aspect of the invention relates to oxidizing 1-chloro-1,2,2,2-tetrafluoroethane, $CHClCF_3$ (HCFC-124) to trifluoroacetyl fluoride, $CF_3COF$ (TFAF), as the predominant acetyl product, which may be accompanied by lesser amounts of one or more of trifluoroacetyl chloride (TFAC) and trifluoroacetic acid (TFAA). Another aspect of the invention relates to oxidizing 1,1-dichloro-2,2-difluoroethane, $CHCl_2CHF_2$ (HCFC-132a), to form a product stream comprising difluoroacetyl fluoride, $CHF_2COF$ (DFAF), difluoroacetyl chloride (DFAC), and the free acid, $CHF_2COOH$ (DFAA).

The polyfluoroacyl fluorides and chlorides are broadly useful as acylating agents for producing agricultural chemicals, pharmaceuticals, industrial products, among other desirable products. The corresponding carboxylic acids are useful as catalysts, intermediates to acid halides, among other products.

BACKGROUND OF THE INVENTION

Gotoh et al., U.S. Pat. No. 5,041,647, discloses oxidizing 1,1-dichloro-2,2,2-trifluoroethane (HCFC-123) with oxygen in the presence of water to trifluoroacetyl chloride (TFAC) accompanied by the free acid (TFAA).

Dittman, U.S. Pat. No. 3,833,407 produces TFAC by reacting HCFC-123 with oxygen in the presence of active radiation.

Jacobson, U.S. Pat. No. 5,241,113 prepares TFAC by oxidizing HCFC-123 with oxygen over a carbon bed in the absence of water.

Childs, U.S. Pat. No. 4,022,824 discloses preparing perfluoro carboxylic acid fluorides by a reaction sequence involving (1) a metathesis reaction between an unfluorinated carboxylic acid and a perfluoroacid fluoride, e.g. trifluoroacetyl fluoride (TFAF), normally prepared by electrofluorinating acetic acid), to obtain the unfluorinated carboxylic acid fluoride, followed by (2) electrofluorinating the acid fluoride product of the metathetical reaction to the desired perfluorocarboxylic acid fluoride.

The disclosure of the previously identified U.S. Patents is hereby incorporated by reference

SUMMARY OF THE INVENTION

This invention provides an oxidative process for preparing polyfluoroacyl fluorides from one or more polyfluoroalkyl substituted chlorofluoromethanes and dichloromethanes.

One aspect of the invention provides perfluoroacyl fluorides and chloroperfluoroacyl fluorides from at least one perfluoroalkyl- and chloroperfluoroalkyl-substituted chlorofluoromethanes.

Another aspect of the invention relates to preparing trifluoroacetyl fluoride from a starting material comprising 1-chloro-1,2,2,2-tetrafluoroethane.

A futher aspect of the invention relates to preparing difluoroacetyl fluoride, among other difluoroacetyl derivatives, from a starting material comprising 1,1-dichloro-2,2-difluoroethane.

The invention comprises a process for preparing polyfluoroacyl fluorides having the formula $X(CF_2)n$ COF. The process comprises contacting at least one polyfluoroalkyl dihalomethane having the formula $X(CF_2)n$ CHClY with a source of oxygen, typically in the substantial absence of water, under conditions effective to produce said acyl fluorides, wherein X is H, Cl or F, n is 1 to 4, usually 1, and Y is Cl or F, with the proviso that when Y is Cl, X is H.

Normally, the temperature and pressure are such that the starting material(s) are at or above the critical point, e.g., the supercritical region.

In some cases X is F and n=1, and the acylfluoride comprises trifluoroacetyl fluoride, $CF_3COF$ (TFAF), which may be accompanied by at least one of trifluoroacetyl chloride $CF_3COCl$ (TFAC), and trifluoroacetic acid, $CF_3COOH$ (TFAA). Normally, TFAF is the predominate product at a selectivity of at least about 50%. For example, this aspect of the invention can produce a product stream comprising at least about 60–70 mole % TFAF, about 5 to 15 mole % TFAC, about 10 to 20 mole % TFAA, about 5 to 10 mole % ($CF_3CFClCFClCF_3$), and about 1 to 5 mole % ClC(0)F.

In some cases X is H and n=1 so that the acyl fluoride produced comprises difluoroacetyl fluoride, $CF_2HCOF$ (DFAF), which may also be accompanied by at least one of difluoroacetyl chloride (DFAC), difluoroacetic acid, $CHF_2COOH$ (DFAA), and $HCF_2CCl_3$. Normally, DFAF, DFAC and DFAA when taken together are produced at selectivities corresponding to at least about 50%. For example, this aspect of the invention can produce a product stream comprising about 40 to 70 mole % of at least one perhaloacetyl selected from the group of DFAC, DFAF and DFAA, about 10 to 15 mole % $CF_2HCCl_3$, about 4 to 10 mole % phosgene, and the remainder, if any, comprises at least one member from the group of HF, $CO_2$ and water.

By "supercritical region", it is meant that combination of temperature and pressure at which the density and other physical properties of the liquid and vapor phases become identical.

The inventive process is normally practiced in the substantial absence of water. By the term "in the substantial absence of water", it is meant that the amount of water present in the conversion or reaction medium as well as the starting materials is limited to that present in the starting materials, and water that may be produced in situ as a byproduct of the overall oxidation; especially when considering that the organic reactants contain chemically-bound hydrogen. Typically, the medium will contain less than about 100 ppm water. The substantial absence of water can permit the inventive process to be practiced in a manner that minimizes hydrolysis of the starting materials and/or products. It will, however, be appreciated by those skilled in this art that TFAF, TFAC, DFAF, DFAC, among other products that are obtained by the present process, may be further hydrolyzed with water to produce TFAA and DFAA.

The instant invention is an improvement in this art in that it avoids the need for a source of active radiation and eliminates the need for water or a catalyst, e.g., conventional processes employed water as a catalyst. Without wishing to be bound by any theory or explanation, it is believed that the presence of water can hydrolyze the instant products to their corresponding acids; such acids typically are not as useful for acylating agents when perhaloacylating amines and alcohols, e.g., to form amides and esters. This invention also provides a method for producing at least one of TFAF, DFAF, and related products in which the product can be separated readily from side products and unreacted starting materials, in a highly pure form, e.g., about 96 to about 99 wt % pure. This method also exhibits increased selectivity and conversion to TFAF without the concomitant formation of substantial amounts of TFAA.

DETAILED DESCRIPTION

The inventive process broadly comprises contacting at least one starting material as defined herein with oxygen at temperatures and pressures and for times effective to produce the desired acyl product(s). An example of the inventive process is exemplified in the following reaction relating to preparing trifluoroacetyl fluoride (equation 1):

$$CF_3CHClF + \tfrac{1}{2} O_2 \rightarrow CF_3COF + HCl \qquad (1)$$

Without wishing to be bound by any theory or explanation, it is believed that the presence of $CF_3COCl$ in the product may be accounted for by competitive side reactions (equations 2 and/or 3 below):

$$CF_3CHClF + \tfrac{1}{2} O_2 \rightarrow CF_3COCl + HF \qquad (2)$$

$$CF_3COF + HCl \rightarrow CF_3COCl + HF \qquad (3)$$

It is also believed that the reactions leading to DFAF from $CHF_2CHCl_2$ may be the result of the following in situ occurrences:

(a) Oxidation of HCFC-132a to DFAC, viz.
$CHF_2CHCl_2 + \tfrac{1}{2} O_2 \rightarrow CHF_2COCl + HCl$;

(b) Oxidation decomposition of $CHF_2CHCl_2$ or $CHF_2COCl$ to produce HF and $H_2O$; and (c) reaction of DFAC with HF to form DFAF, viz. $CHF_2COCl + HF \rightarrow CHF_2COF + HCl$.

The aforementioned DFAF reactions may occur in any expedient sequence. It is further believed that the appearance of DFAA in the product mixture may be explained by in situ hydrolysis of DFAC or DFAF by the $H_2O$ oxidation side product, e.g., $CHF_2COX + H_2O \rightarrow CH_2FCOOH + HX$, where x=Cl or F.

Examples of other polyfluoroalkyl dihalomethane starting materials (and isomers thereof) and the polyfluoroacyl products that may be prepared therefrom in accordance with the inventive method are tabulated below:

| Starting Material | Polyacyl Products |
|---|---|
| $CClF_2CHClF$ (HCFC-123a) | $CClF_2COY$, Y=F, Cl, OH |
| $CHF_2CF_2CF_2CHClF$ (HCFC-235CA) | $CHF_2CF_2CF_2COY$, Y=F, Cl, OH |
| $CClF_2CF_2CHClF$ (HCFC-225CB) | $CClF_2CF_2COY$, Y=F, Cl, OH |
| $CHF_2CHClF$ (HCFC-133) | $CHF_2COY$, Y=F, Cl, OH |
| $CF_3CF_2CHClF$ (HCFC-226CA) | $CF_3CF_2COY$, Y=F, Cl, OH |

The most significant process parameters for carrying out the reaction are temperature, pressure, and time. Normally, the higher the temperature or pressure, the shorter the time required to achieve an acceptable conversion. The reaction may be carried out in a temperature range of about 190° to about 320° C., and at pressures from about 400 to about 2,500 psig. Typically, temperatures of about 190° to 300° C. and pressures of about 800 to 2,000 psig are employed. At temperatures and pressures below the aforementioned range, the conversion rate is relatively slow. At temperatures greater than those previously identified, the reaction conditions must be controlled to avoid side reactions which can lower the selectivity to TFAC. Pressures above the previously identified range may be employed; but the equipment costs would be higher. If desired, the reaction can be performed at relatively high temperatures by employing much shortened reaction times. Exemplification of suitable reaction times is provided hereinafter. While the specific reaction time for making a desired product will vary subject to the reaction variables identified herein, typically the reaction time will be about 10 to about 90 minutes.

While any suitable ratio of oxygen can be employed, normally the mole ratio of oxygen to the material to be oxidized can ranges from about 0.1 to about 1, with a ratio of 0.2 to 0.8 being desirable. Oxygen to oxidizable material ratios above about 1 tend to fall within the explosive range and would not be preferred. Oxygen to oxidizable material ratios below about 0.5 may reduce the desired product formation rate such that it becomes desirable to recycle unreacted starting material. The oxygen is normally diluted with one or more gases, which are inert to the oxidation environment, such as nitrogen, argon, among others, so as to keep the reaction mixture out of the explosive range and to avoid exotherms which could decompose the polyfluoroacylfluoride product(s). While any suitable oxygen source can be employed, molecular oxygen, dried air or mixtures thereof with an inert gas can be used to practice the invention.

A reactor resistant to corrosion by reaction by-products such as hydrogen fluoride, as well as chlorine and water which can come from the reaction of byproduct hydrogen chloride and oxygen, is required.

Materials useful for the reactor surfaces include silver, nickel, tantalum, nickel based alloys sold under the trademarks HASTELLOY® INCONEL® among others. Stainless steel such as 316 is typically unsatisfactory as it causes many byproducts to be produced, and its use results in decreased selectivity and conversions. Glass can be severely etched and, therefore, is not practical. ALLOY C276 sold under the trademark HASTELLOY® 276 and ALLOY 600 sold under the trademark INCONEL® are the preferred reactor materials since they exhibit minimal corrosion, and selectivity of the desired product is consistently high.

The acyl fluoride products are isolated by any suitable standard procedure such as distillation. When the product boils below room temperature, the distillation may be carried out under pressure. For example, the purification of TFAF may be achieved by distillation under pressure using a 20 plate Oldershaw column or equivalent. Typically, TFAF is recovered by using a distillation temperature of less than about −60° C. whereas TFAC is recovered by using a distillation temperature of less than about −20° C.

The inventive oxidation process may be carried out either in a batch or continuous fashion. In either case, the process is performed in a manner sufficient to cause the oxygen and raw material to contact and form the desired product. For example, when practicing a continuous process, oxygen and at least one raw material are introduced, for example, simultaneously into a reactor. When practicing a batch process, oxygen is introduced into a reactor containing at least one raw material. In each case conditions, which are not in the explosive range for the mixture of oxygen and the material to be oxidized, are preferred.

Depending upon the desired product, the stream exiting the reactor can be recovered as a useful product, separated into its components, at least a portion recycled to the reactor, among other processing steps. An increase in the relative amount of an inert component in the starting material will in turn increase the amount of unconverted material that exits the reactor.

While the above description places particular emphasis upon oxidizing certain starting materials, the inventive process can be practiced by using any suitable raw material. Normally, the raw material will be commercially available and about 90 to about 98 % by wt. pure.

The following Examples serve to illustrate the invention, but are not intended to limit the scope of the invention.

All analyses reported in the following Examples were obtained by employing conventional gas chromatography (GC) techniques on a Hewlett-Packard Series II 5890 instrument. A 105 m×0.32 mm RTX-I (Restek Corp., Bellefonte, Pa.) capillary column was used with a thermal conductivity detector for measuring the products and byproducts. A temperature program of 40° C. (15 minute hold), heating 16° C./min to 200° C. (10 minute hold), and heating 50° C./min to 250° C. (10 minute hold) was employed during the Examples. "Conversion" and "selectivity" which are used herein are defined as follows. Conversion is the molar % of starting material which was consumed during the inventive oxidation process. Selectivity is defined as:

$$\frac{\text{moles product or byproduct}}{\text{moles starting material comsumed}} \times 100\%$$

EXAMPLE 1

TFAF

A 400cc Hastelloy ® C-276 bomb was charged with approximately 68.2 g (0.5 mole) HCFC-124, and perfluoroctane as an internal standard for GC analyses. The bomb was closed and its contents were heated to about 230° C. and about 600 psi pressure. Four about 200 psi injections of air from an auxiliary bomb were added at 5 minute intervals. After the final injection, the bomb was heated to a temperature of about 230° C. for an additional 15 minutes to give a final pressure of about 1900 psi. The bomb was cooled to approximately −85° C. before the air and HCl were vented to a caustic scrubber. The liquid contents were analyzed by gas chromatography using a high pressure syringe for sampling. The analyses indicated about 38% HCFC-124 conversion (95% conversion based on air) to a selectivity of 66% TFAF, 6% TFAC, 16% TFAA, 1% ClC(O)F and 7% ($CF_3CFCCFClCF_3$).

EXAMPLE 2

Difluoroacetyls

A 400cc Hastelloy® C-276 bomb was charged with approximately 134.9 g (1.0 mole) of HCFC-132a ($CF_2HCHCl_2$), and carbon tetrachloride as an internal standard for gas chromatography analyses. The bomb was closed and its contents were heated to about 200° C. and 450 psi pressure.

Four 100 psi injections of oxygen from an auxiliary bomb were injected at 15 minute intervals to give an approximate one hour reaction time The bomb was cooled to about −85° C. by using dry ice before HCl and any remaining oxygen were vented to a caustic scrubber. The liquid contents remaining in the bomb were analyzed by gas chromatography and showed a 46% HCFC-132 a conversion to a selectivity of 15% DFAC, 15% DFAF, 24% DFAA, 13% $CF_2HCCl_3$, and 6% phosgene. If desired, the product mixture comprising DFAF, DFAC, and DFAA can be hydrolyzed to DFAA by using known technology.

I claim:

1. A process for preparing polyfluoroacyl fluorides having the formula X($CF_2$)nCOF comprising contacting at least one polyfluoroalkyldihalomethane having the formula X($CF_2$)nCHClY with an oxygen source in the substantial absence of water to form a mixture, wherein said mixture is heated at a temperature in the range of about 190 to 320° C. at a pressure in the range of about 400 to 2,500 psi to obtain said acyl fluorides, wherein X is H, Cl or F, n is 1 to 4, and Y is Cl or F, with the proviso that when Y is Cl, X is H.

2. The process of claim 1, wherein X is F, n is 1 and the acyl product comprises trifluoroacetyl fluoride.

3. The process of claim 2 wherein the product comprises trifluoroacetyl fluoride and at least one of trifluoroacetyl chloride and trifluoroacetic acid.

4. The process of claim 2 wherein the process has a selectivity of at least about 50 percent and forms a product comprising trifluoroacetyl fluoride.

5. The process of claim 1 wherein X is H and n is 1 and the product comprises difluoroacetyl fluoride.

6. The process of claim 5 wherein the product comprises difluoroacetyl fluoride and at least one of difluoroacetyl chloride and difluoroacetic acid.

7. The process of claim 6 wherein the process has a selectivity of at least about 50 percent.

8. The process of claim 7 wherein the product further comprises $CHF_2CCl_3$.

9. The process of claim 1 or wherein at least a portion of said mixture is recycled to said contacting.

10. The process of claim 1 wherein said polyfluoroalkyldihalomethane comprises at least one member from the group consisting of $CClF_2CHClF$ (HCFC-123a), $CHF_2CF_2CF_2CHClF$ (HCFC-235CA), $CClF_2CF_2CHClF$ (HCFC-225CB), $CHF_2CHClF$ (HCFC-133), and $CF_3CF_2CHClF$ (HCFC-226CA).

11. The process of claim 10 wherein said halide comprises at least one member from the group consisting of $CClF_2COY$, Y=F, Cl, OH; $CHF_2CF_2CF_2COY$, Y=F, Cl, OH; $CClF_2CF_2COY$, Y=F, Cl, OH; $CHF_2COY$, Y=F, Cl, OH; and $CF_3CF_2COY$, Y=F, Cl, OH.

12. The process of claims 1, wherein said polyfluoroalkyldihalomethane comprises 1-chloro-1,2,2,2-tetrafluoromethane (HCFC-124).

* * * * *